(12) United States Patent
Hamrick

(10) Patent No.: US 12,297,423 B2
(45) Date of Patent: May 13, 2025

(54) CONTAMINATION CONTROL WHEN GROWING YEASTS

(71) Applicant: Edward Brian Hamrick, Sunny Isles Beach, FL (US)

(72) Inventor: Edward Brian Hamrick, Sunny Isles Beach, FL (US)

(*) Notice: Subject to any disclaimer, the term of this patent is extended or adjusted under 35 U.S.C. 154(b) by 0 days.

(21) Appl. No.: 18/532,043

(22) Filed: Dec. 7, 2023

(65) Prior Publication Data
US 2025/0066714 A1 Feb. 27, 2025

Related U.S. Application Data

(60) Provisional application No. 63/534,123, filed on Aug. 23, 2023.

(51) Int. Cl.
*C12N 1/18* (2006.01)
*C12M 1/02* (2006.01)
*C12N 1/02* (2006.01)
*C12P 7/08* (2006.01)
*C12R 1/85* (2006.01)

(52) U.S. Cl.
CPC ............ *C12N 1/185* (2021.05); *C12M 41/18* (2013.01); *C12N 1/02* (2013.01); *C12P 7/08* (2013.01); *C12N 2500/46* (2013.01); *C12R 2001/85* (2021.05)

(58) Field of Classification Search
None
See application file for complete search history.

(56) References Cited

U.S. PATENT DOCUMENTS 2,230,318 A 2/1941 Firmin

OTHER PUBLICATIONS

Yue, G. et al. "The influence of nitrogen sources on ethanol production by yeast from concentrated sweet sorghum juice". Biomass and Bioenergy, vol. 39 (2012), pp. 48-52. (Year: 2012).*
Grant, C.L. "Minor element composition of yeast extract" .Journal of Bacteriology, vol. 84 (1962), pp. 869-870 (Year: 1962).*
Infante, C.J. et al. "Removal of lead, mercury and nickel uising the yeast Saccharomyces cerevisiae". Revista MVZ Cordoba, vol. 19 , No. 2 (2014), pp. 4141-4149) (Year: 2014).*
East Biotech Company website—retrieved Mar. 8, 2024. URL[ http:// www.eastbio.net/products/] (Year: 2019).*
The Shine Heating Website, retrieved on Mar. 8, 2024, Welded Spiral Plate Heat Exchanger (shineheating.com); [ URL [https:// www.shineheating.com/spiralwound-p00020p1.html]; 2019) ] (Year: 2019).*
Wang, A. et al. "Comparison of different options for harvest of a therapeutic protein product from high cell density yeast fermentation broth." Biotechnology and Bioengineering, vol. 94, No. 1 (May 5, 2006), pp. 91-104 (Year: 2006).*
Wongsurakul, P. et al."Comprehensive review on potential contamination in fuel ethanol production with proposed specific guideline criteria" Energies, vol. 15 (2022), p. 2986 (Year: 2022).*
Mazzei, L. et al. "The structure-based reaction mechanism of urease, a nickel dependent enzyme: tale of a long debate". Journal of Biological Inorganic Chemistry, vol. 25 (2020), pp. 829-845 (Year: 2020).*
Piquero-Casals, J. et al. "Urea in Dermatology: A review of its emollient, moisturizing, keratolytic, skin barrier enhancing and antimicrobial properties". Dermatol. Ther. (Heidelb), vol. 11 (2021), pp. 1905-1915 (Year: 2021).*
Benoit, S.L. et al. "Nickel chelation therapy as an approach to combat multi-drug resistant enteric pathogens". Scientific Reports, vol. 9 (2019), p. 13851 (Year: 2019).*
Narendranath, N.V. et al. "Urea Hydrogen Peroxide reduces the numbers of Lactobacilli, nourishes yeast, and leaves no residues in the ethanol fermentation". Applied and Environmental Microbiology, vol. 66, No. 10 (2000), pp. 4187-4192. (Year: 2000).*
Narendranath, N.V. et al. "Effects of Lactobacilli on yeast-catalyzed ethanol fermentations". Applied and Environmental Microbiology, vol. 63, No. 11 (1997), pp. 4158-4163. (Year: 1997).*
Gramss, G. "Control of heavy metals from Barley and wheat grains during malting and brewing". Advances in Nutrition and Food Science, Issue 5 (2020), pp. 1-9. (Year: 2020).*
Kebede, A. et al. "The effect of container type on the growth of yeast and lactic acid bacteria during production of Sethemi, South African spontaneously fermented milk." Food Research International, vol. 40 (2007), pp. 33-38. (Year: 2007).*
Speers, R.A. et al. "Colloidal properties of flocculent and nonflocculent Brewing yeasts suspensions" Biotechnology Progress, vol. 9 (1993), pp. 267-272. (Year: 1993).*
Beckner, M. et al. "Microbial contamination of fuel ethanol fermentations". Letters in Applied Microbiology. vol. 53 (2011), pp. 387-394 (Year: 2011).*
Martins da Matta, V. et al. "A new method for yeast recovery in batch ethanol fermentations: filter aid filtration followed by separation of yeast from filter aid using hydrocyclones". Bioseparation, vol. 9 (2000), pp. 43-53 (Year: 2000).*

(Continued)

*Primary Examiner* — Anna Skibinsky
*Assistant Examiner* — Alexandra Geraldine Dace Denito
(74) *Attorney, Agent, or Firm* — O'Connor & Company; Ryan P. O'Connor

(57) ABSTRACT

A method for contamination control when growing yeasts is provided. Bacterial contamination is controlled by using urea as the primary nitrogen source while simultaneously limiting the amount of nickel available to contaminating bacteria. Bacteria require nickel as a cofactor for urease enzymes in order to use urea for growth while yeasts do not require nickel as a cofactor for any enzymes. Nickel is limited by using titanium in plate heat exchangers instead of stainless steel. Ethyl carbamate is limited by using a carbon/nitrogen ratio that consumes all urea during fermentation and by separating co-products after fermentation and before distillation. Yeast recycling is performed by using either single-step or two-step centrifugation, without acid washing. This method enables yeast recycling with sugarcane ethanol and sugar beet ethanol production. This method also enables yeast recycling with corn ethanol and grain ethanol production with coproduct recovery after fermentation and before distillation.

6 Claims, No Drawings

(56) References Cited

OTHER PUBLICATIONS

Vlotman, D. et al. "Shear enhanced flotation separation technology in winery wastewater treatment". Water, vol. 15 (Jun. 2023), p. 2409 (Year: 2023).*

Inskeep et al., "Food yeast from sulfite liquor", Industrial & Engineering Chemistry 43.8 (1951): 1702-1711.

Narendranath et al., "Urea hydrogen peroxide reduces the numbers of lactobacilli, nourishes yeast, and leaves no residues in the ethanol fermentation", Applied and Environmental microbiology 66.10 (2000): 4187-4192.

Jones et al., "Fuel alcohol production: optimization of temperature for efficient very-high gravity fermentation", Applied and environmental microbiology 60.3 (1994): 1048-1051.

Whiting et al., "Detection of *Pediococcus* spp. in brewing yeast by a rapid immunoassay", Applied and environmental microbiology 58.2 (1992): 713-716.

Prins et al., "A buffered media system for yeast batch culture growth", BMC microbiology 21.1 (2021): 1-9.

Strope, Pooja K., et al., "Molecular evolution of urea amidolyase and urea carboxylase in fungi", BMC Evolutionary Biology 11.1 (2011): 1-15.

Bassi et al., "Interaction of *Saccharomyces cerevisiae*-Lactobacillus fermentum-Dekkera bruxellensis and feedstock on fuel ethanol fermentation", Antonie Van Leeuwenhoek 111 (2018), Abstract.

Gao et al., "Determination of an economical medium for growth of Lactobacillus fermentum using response surface methodology", Letters in applied microbiology 49.5 (2009), Abstract.

Olendorff et al., "Survey of antibiotics residues in DDGS from 14 different states by LCM", Cereal Chemistry 98.1 (2021), Abstract.

Yang, et al., "Comparisons of urea or ammonium on growth and fermentative metabolism of *Saccharomyces cerevisiae* in ethanol fermentation", World Journal of Microbiology and Biotechnology 37.6 (2021), Abstract.

* cited by examiner

CONTAMINATION CONTROL WHEN GROWING YEASTS

PRIORITY DATA

This patent application is a non-provisional application claiming priority to U.S. Provisional Patent App. No. 63/534,123, filed on Aug. 23, 2023, which is hereby incorporated by reference herein for all purposes.

FIELD OF THE INVENTION

The present invention pertains to growth of microorganisms. More specifically, this invention pertains to contamination control when growing yeasts.

BACKGROUND OF THE INVENTION

Industrial-scale growth of yeasts is commonly used to make single cell protein (SCP) or coproducts such as ethanol. This growth is herein referred to as 'fermentation' and uses a 'fermenter' to grow these yeasts, even when there are no coproducts such as ethanol, and even when the process is either aerobic or anaerobic.

One problem with growing yeasts at an industrial scale, such as in fermenters with a volume of more than 100 m$^3$, is contamination by other microorganisms.

For instance, industrial-scale fermenters using *Saccharomyces cerevisiae* to produce ethanol from sugars are often contaminated by lactic acid bacteria such as *Lactobacillus fermentum* or by wild yeasts such as *Dekkera bruxellensis* and its anamorph *Brettanomyces bruxellensis*. Contamination is especially common when yeast is recycled. This contamination is described in Bassi, Ana Paula Guarnieri, et al., "Interaction of *Saccharomyces cerevisiae*-*Lactobacillus fermentum*-*Dekkera bruxellensis* and feedstock on fuel ethanol fermentation", *Antonie Van Leeuwenhoek* 111 (2018): 1661-1672, which is hereby incorporated by reference.

Contamination occurs when the growth rate of an undesired microorganism is higher than the growth rate of a desired microorganism. For instance, the doubling time of most lactic acid bacteria is about 0.5 hours and the doubling time of many yeasts is about 1.5 hours. This means that over a 24-hour period, a single bacterial cell of lactic acid bacteria grows to $2^{24/0.5}$ or $3 \times 10^{14}$ cells, whereas a single yeast cell grows to $2^{24/1.5}$ or $7 \times 10^4$ cells. Reducing the growth rate of lactic acid bacteria to slightly less than that of a yeast (increasing the doubling time to just a bit more than 1.5 hours) completely eliminates the problem of contamination, even over many months of continuous fermentation. Often forgotten is that increasing the growth rate of yeast (e.g., by using urea as the nitrogen source) also reduces contamination.

Contamination control is directly related to the time of fermentation and the initial concentration of undesired microorganisms and desired microorganisms, and to the growth rate of these organisms. Simple calculations show that longer fermentations have more of a problem with contamination than shorter fermentations, factoring in the different growth rates of these microorganisms.

Therefore, contamination can be controlled by a combination of reducing the fermentation time (e.g., yeast recycling when making fuel ethanol in Brazil), killing contaminating microorganisms (e.g., washing recycled yeast with sulphuric acid), or reducing the growth rate of contaminating microorganisms (e.g., with antibiotics).

Industrial-scale growth of yeasts is necessarily performed in non-aseptic conditions since industrial-scale aseptic growth is prohibitively expensive. The most common methods of contamination control in industrial-scale fermentation have been the use of sulfites ($SO_2$), antibiotics and peroxides.

Winemakers in ancient Rome burned sulfur candles in wine containers to control contamination that turned wine to vinegar, currently known to be caused by acetic acid bacteria such as *Acetobacter aceti*. Today, sulfites are often used to prevent bacterial growth in winemaking. However, sulfites cause allergic reactions in some people, and wine labels must have warnings that the wine contains sulfites.

The first successful industrial-scale fermentation of SCP was performed in Germany in the 1930s and 1940s using waste liquor from sulfite pulping. This is described in Inskeep, Gordon C., et al., "Food yeast from sulfite liquor", *Industrial & Engineering Chemistry* 43.8 (1951): 1702-1711, which is hereby incorporated by reference. Inskeep notes that "The yeast fermentation has been remarkably free from contamination. In more than 2 years of operation of the Lake States plant, production has never been interrupted because of contamination. The conditions of pH, temperature, and aeration with agitation permit the propagation of *T. utilis* at rates rapid enough to overgrow and prevent the development of foreign organisms." Inskeep also notes that "The pH of the fermentation mixture (wort) runs about 5.0." It seems that Inskeep didn't consider that residual sulfites from pulping probably caused the lack of bacterial contamination. Also, in the 1950s, allergic reactions to sulfites weren't known.

Fuel ethanol producers today often use antibiotics to control bacterial contamination in industrial-scale fermentation. However, this is expensive. Additionally, the valuable coproduct of dried distiller's grains with solubles (DDGS) is contaminated by these antibiotics which enter the food chain, leading to antibiotic-resistant bacteria which cause illnesses in people. This is described in Olendorff, Samantha A., Karolina Chmielewska, and Kevin R. Tucker, "Survey of antibiotics residues in DDGS from 14 different states by LCM", *Cereal Chemistry* 98.1 (2021): 81-88, which is hereby incorporated by reference.

Attempts have been made to control bacterial contamination using urea hydrogen peroxide and nitrogen-free peroxygen-releasing compounds. The use of urea hydrogen peroxide to control *lactobacillus* contamination is described in Narendranath, N. V., K. C. Thomas, and W. M. Ingledew, "Urea hydrogen peroxide reduces the numbers of lactobacilli, nourishes yeast, and leaves no residues in the ethanol fermentation", *Applied and Environmental microbiology* 66.10 (2000): 4187-4192, which is hereby incorporated by reference. The use of nitrogen-free peroxygen-releasing compounds to control bacterial contamination is described by Solomon in U.S. Pat. No. 8,759,051, issued on Jun. 24, 2014, which is hereby incorporated by reference. However, the use of peroxides to control bacterial contamination has been shown to be uneconomical and is not widely used today in industrial-scale fermentation processes.

Four microorganisms have been used for more than 30 years to make SCP that can be safely consumed by people and fed to animals. A yeast that has been used to make SCP from hexose sugars and from hydrolyzed starch for more than 100 years is *Saccharomyces cerevisiae*, more commonly known as baker's yeast, brewer's yeast or just yeast. A yeast that has been used to make SCP from hydrolyzed starch, hexose sugars and pentose sugars for more than 80 years is *Cyberlindnera jadinii*, more commonly known as

*Candida utilis* or Torula. A yeast that has been used to make SCP from hydrolyzed starch, hexose sugars, lactose and galacturonic acid for more than 50 years is *Kluyveromyces marxianus*, also known as *Candida kefyr* and *Kluyveromyces lactis*. A yeast that has been used to make SCP from lipids (oils) for more than 50 years is *Yarrowia lipolytica*.

All four of these yeasts have been recognized in the United States as Generally Recognized as Safe (GRAS) and have received similar approvals in many other countries, including Canada, Europe, Australia, China and Russia. All have been extensively tested and shown to be safe in animal feed (especially fish and chicken) and for human consumption. *Candida utilis* (Torula) is even commonly used today as a flavor enhancer—it has an umami (meaty) flavor and tastes good.

Bacterial contamination is often the biggest technical problem when using yeasts in industrial-scale fermentation to produce ethanol, single-cell protein and Omega-3 lipids.

The need exists for industrial-scale contamination control without using sulfites, antibiotics, acid washes, or peroxides when producing fuel ethanol and when growing yeasts for SCP.

SUMMARY OF THE INVENTION

The invention in some variations provides a method for growing yeasts, the method comprising growing yeasts for a fermentation time at a starting pH in a fermentation broth containing a carbon source, a nitrogen source, and a mineral source, wherein the fermentation broth is in operable communication with a heat exchanger, wherein the yeasts belong to the class *Saccharomyces*, wherein the nitrogen source in the fermentation broth comprises urea, wherein the amount of nickel in the fermentation broth is less than 1 mg/kg, and wherein the urea is introduced to the fermentation broth such that the pH of the fermentation broth during the fermentation time does not exceed the starting pH by more than 2.0.

In preferred embodiments, the heat exchanger is a plate heat exchanger comprising titanium heat exchange plates, wherein the titanium heat exchange plates contain less than 1 g/kg nickel.

In preferred embodiments, the heat exchanger is a spiral plate heat exchanger comprising titanium heat exchange plates, wherein the titanium heat exchange plates contain less than 1 g/kg nickel.

In preferred embodiments, the method produces ethanol in the fermentation broth.

In preferred embodiments, the ratio of the amount of the carbon source to the amount of the urea is such that essentially no urea remains in the fermentation broth before the ethanol is separated from the fermentation broth by distillation.

In preferred embodiments, the method uses separation of the yeasts from the fermentation broth to produce recycled yeasts, and wherein the recycled yeasts are not washed with acid after the separation.

In preferred embodiments, the separation uses centrifugation that receives an input liquid and produces output solids and a supernatant, wherein the input liquid is the fermentation broth, wherein the centrifugation has a cut size between 1.5 microns and 2.5 microns, and wherein the output solids comprise the recycled yeast.

In some embodiments, the yeasts comprise non-flocculated yeasts, wherein the separation uses a first centrifugation and a second centrifugation, wherein the first centrifugation receives a first input liquid and produces a first output solids and a first supernatant, wherein the second centrifugation receives a second input liquid and produces a second output solids and a second supernatant, wherein the first input liquid is the fermentation broth, wherein the first centrifugation has a cut size between 10 microns and 15 microns, wherein the first output solids are fermentation coproducts, wherein the first supernatant is the second input liquid, wherein the second centrifugation has a cut size between 1.5 microns and 2.5 microns, and wherein the second output solids are the recycled yeasts.

In some embodiments, the yeasts comprise flocculated yeasts, wherein the separation uses a high-shear deflocculation, a first centrifugation and a second centrifugation, wherein the high-shear deflocculation receives a high-shear input liquid and produces a high-shear output liquid, wherein the first centrifugation receives a first input liquid and produces a first output solids and a first supernatant, wherein the second centrifugation receives a second input liquid and produces a second output solids and a second supernatant, wherein the high-shear input liquid is the fermentation broth, wherein the Kolmogorov length scale of the high-shear deflocculation is between 7 microns and 15 microns, wherein the first input liquid is the high-shear output liquid, wherein the first centrifugation has a cut size between 10 microns and 15 microns, wherein the first output solids are fermentation coproducts, wherein the first supernatant is the second input liquid, wherein the second centrifugation has a cut size between 1.5 microns and 2.5 microns, and wherein the second output solids are the recycled yeasts.

DETAILED DESCRIPTION OF EMBODIMENTS OF THE INVENTION

The methods, processes, and systems of the present invention will be described in detail by reference to various non-limiting embodiments and figure(s).

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing parameters, conditions, results, and so forth used in the specification and claims are to be understood as being modified in all instances by the term "about." Accordingly, unless indicated to the contrary, the numbers set forth in the following specification and attached claims are approximations that may vary depending upon specific algorithms and calculations.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except in the case of Markush groups. Thus in some embodiments not otherwise explicitly recited, any instance of "comprising" may be replaced by "consisting of" or, alternatively, by "consisting essentially of."

No embodiments described herein shall be limited by any theory or speculation regarding reaction mechanisms, mass-transfer mechanisms, or descriptions of feedstocks or products.

The present invention is premised on a technical solution to the serious problem of bacterial contamination during yeast growth. It has been recognized by the present inventor that bacteria require nickel as a cofactor for urease enzymes in order to use urea for growth, while yeasts do not require nickel as a cofactor for any enzymes. This principle is applied by designing a fermentation system in which nickel content is minimized in the broth, while at the same time, urea is the primary nitrogen source—which therefore reduces the growth rate of bacteria below the growth rate of yeast, preventing contamination.

Many bacteria, especially many which often contaminate yeast fermentations, do not contain urease enzymes and thus can't grow at all when urea is the nitrogen source. These bacteria include Liquorilactobacillus *vini* (*Lactobacillus vini*), *Lactobacillus plantarum*, *Lactobacillus brevis*, and *Lactobacillus casei*. However, two common contaminating bacteria which do contain urease enzymes are *Lactobacillus fermentum* and *Lactobacillus reuteri*. In this disclosure, the contamination by these organisms is controlled by reducing the amount of nickel in the fermentation broth.

Reducing the amount of nickel in the fermentation broth has been shown to significantly reduce the growth rate of bacteria in the fermentation broth. Since nickel is a catalyst for urease in bacteria, reducing the concentration of nickel by half reduces the growth of bacteria by half when urea is the primary nitrogen source.

An additional contributor to contamination control is simply using urea as the primary nitrogen source. *Lactobacillus fermentum* grows slower on urea than ammonium. This is described in Gao, X., S. Y. Qiao, and W. Q. Lu., "Determination of an economical medium for growth of *Lactobacillus fermentum* using response surface methodology", *Letters in applied microbiology* 49.5 (2009): 556-561, which is hereby incorporated by reference. Many yeasts, such as *Saccharomyces cerevisiae*, grow faster on urea than other nitrogen sources. This is described in Jones, Alison M., and W. M. Ingledew., "Fuel alcohol production: optimization of temperature for efficient very-high-gravity fermentation", *Applied and environmental microbiology* 60.3 (1994): 1048-1051, which is hereby incorporated by reference.

A contributor to contamination control when using yeast recycling is by using differential centrifugation to separate yeast from bacteria and recycling the yeast. This was first described in Whiting, M., et al., "Detection of *Pediococcus* spp. in brewing yeast by a rapid immunoassay", *Applied and environmental microbiology* 58.2 (1992): 713-716, which is hereby incorporated by reference. The g-forces used by Whiting show separation of flocculated yeast cells from bacterial cells. Yeast cells are about 7 microns in size, while bacteria are about 1 micron in size, with similar densities, so the Stokes settling velocities differ by a factor of about 50, with yeast cells setting about 50 times faster than bacteria. This is complicated by the presence of solids (coproducts) in corn ethanol production, but yeast can be separated from these solids by centrifuging once to remove the solids and a second time to separate the yeast. This is complicated by flocculation, which can be solved by using a non-flocculating yeast such as *Saccharomyces cerevisiae* PE-2 or by using a high-shear mixer to deflocculate before centrifugation.

A complication when using urea with yeasts is that when there is too much urea inside yeast cells, they will excrete ammonium to relieve ammonium toxicity, and bacteria grow well on ammonium. When the concentration of urea is less than 0.25 mM, the urea enters the yeast cell by an inducible urea permease and above 0.5 mM, the urea enters the yeast cell by facilitated diffusion. This is described in Yang, Xinchao, et al., "Comparisons of urea or ammonium on growth and fermentative metabolism of *Saccharomyces cerevisiae* in ethanol fermentation", *World Journal of Microbiology and Biotechnology* 37.6 (2021): 98, which is hereby incorporated by reference. If this diffusion rate is higher than the kinetic need for nitrogen for growth, yeast cells will detoxify themselves of ammonium from urea by excreting ammonium. This is described in Prins, Rianne C., and Sonja Billerbeck., "A buffered media system for yeast batch culture growth", *BMC microbiology* 21.1 (2021): 1-9, which is hereby incorporated by reference. Prins shows that growth of yeast with urea as the primary nitrogen source leads to alkalinization at 5 mM urea (Prins, FIGS. 1A and 1B, left columns, unbuffered). Alkalinization is due to excretion of ammonia from yeasts. The present inventor has demonstrated experimentally that alkalinization is reduced by fed-batch addition of urea, keeping the concentration of urea below 1 mM—significantly reducing the growth rate of contaminating bacteria.

The invention in some variations provides a method for growing yeasts, the method comprising growing yeasts for a fermentation time at a starting pH in a fermentation broth containing a carbon source, a nitrogen source, and a mineral source, wherein the fermentation broth is in operable communication (i.e., capable of being heat-exchanged) with a heat exchanger, wherein the yeasts belong to the class *Saccharomyces*, wherein the nitrogen source in the fermentation broth comprises urea, wherein the amount of nickel in the fermentation broth is less than 1 mg/kg, and wherein the urea is introduced to the fermentation broth such that the pH of the fermentation broth during the fermentation time does not exceed the starting pH by more than 2.0 (i.e., by more than two units of pH).

When urea is the nitrogen source, bacteria can only grow when there is sufficient nickel in the fermentation broth to catalyze the urease enzyme's conversions of urea to ammonia and $CO_2$. Yeasts use the urea amidolyase enzyme (which is not present in bacteria) to catalyze this conversion of urea to ammonia and $CO_2$. Urea amidolyase uses biotin instead of nickel as a catalyst. This difference between bacteria and yeasts is described in Strope, Pooja K., et al., "Molecular evolution of urea amidolyase and urea carboxylase in fungi", *BMC Evolutionary Biology* 11.1 (2011): 1-15, which is hereby incorporated by reference.

In acidic solutions containing chloride ions, stainless steel leaches nickel into solution. One way to reduce the amount of nickel in the aqueous fermentation broth is to use heat exchangers made from titanium alloys with trace amounts of nickel, or other metal alloys with trace amounts of nickel. Nickel is a trace element in all titanium alloys except for the nitinol alloy, which has about 50% nickel and 50% titanium.

Monitoring the pH compared with the starting pH reveals that when the pH increases, the feed rate of urea is too high, and slowing the fed-batch rate of urea feeding will result in less ammonium being excreted. Bacteria can use ammonium as a nitrogen source, so when less or no ammonium is excreted, the ammonium is not available for the bacteria to consume.

In preferred embodiments, the heat exchanger is a plate heat exchanger comprising titanium heat exchange plates, wherein the titanium heat exchange plates contain less than 1 g/kg nickel. In this specification, "titanium" includes titanium alloys, provided such alloys contain less than 1 g/kg nickel.

In preferred embodiments, the heat exchanger is a spiral plate heat exchanger comprising titanium heat exchange plates, wherein the titanium heat exchange plates contain less than 1 g/kg nickel.

The main source of nickel in a fermenter is from leaching of nickel from the stainless steel in a heat exchanger. The two most practical heat exchangers for fermenters are wide-gap plate heat exchangers and spiral heat exchangers. These heat exchangers are available commercially using titanium instead of stainless steel and don't leach nickel. The added benefit of using heat exchangers made from titanium alloys is that they aren't subject to corrosion when cooling with sea water, which is an inexhaustible and inexpensive cooling source at an industrial scale.

In preferred embodiments, the method produces ethanol in the fermentation broth.

The most widely used yeast for producing ethanol is *Saccharomyces cerevisiae*, which grows well using urea as a nitrogen source, generally using submerged fermentation, normally under anaerobic conditions or slightly aerobic conditions.

In preferred embodiments, the ratio of the amount of the carbon source to the amount of the urea is such that essentially no urea remains in the fermentation broth before the ethanol is separated from the fermentation broth by distillation.

Ethyl carbamate, which is a known carcinogen, is produced by the reaction of urea and ethanol and elevated temperatures, and urea is safe in aerobic growth without ethanol production. Urea hydrogen peroxide does not produce ethyl carbamate unless ethanol is present at higher temperatures and therefore is safely used in tooth whiteners. Preferred variations of the present invention assure that no urea is present during distillation, which eliminates the problem of production of ethyl carbamate during distillation.

In preferred embodiments, the method uses separation of the yeasts from the fermentation broth to produce recycled yeasts, wherein the recycled yeasts are not washed with acid after the separation.

The process for yeast recycling used widely in Brazil for fermenting sugarcane juice and sugarcane molasses is called the Melle-Boinot process, which was patented by Firmin Boinot in 1936 for fermenting sugar beet juice to ethanol. This is described by Boinot in U.S. Pat. No. 2,230,318, issued on Feb. 4, 1941, which is hereby incorporated by reference. The Melle-Boinot process involves separating yeasts and bacteria after fermentation using centrifugation, followed by a dilute sulphuric acid treatment which kills the bacteria without killing much of the yeast. However, this process is expensive, uses dangerous acids and causes problems with disposal of the effluent after treatment. By contrast, the present invention eliminates the need for acid treatment after separation of yeast, since the growth rate of bacteria is slowed by the techniques described above.

In preferred embodiments, the separation uses centrifugation that receives an input liquid and produces output solids and a supernatant, wherein the input liquid is the fermentation broth, wherein the centrifugation has a cut size between 1.5 microns and 2.5 microns, and wherein the output solids comprise the recycled yeast.

Using this cut size separates yeast from the fermentation broth, since yeasts generally are larger than 2.5 microns in diameter. This embodiment is used when there aren't coproducts larger than 2.5 microns in diameter that need to be separated from yeast. This is true for sugarcane juice, sugarcane molasses, sugar beet juice and sugar beet molasses, since these have already been centrifuged to remove solids.

In some embodiments, the yeasts comprise non-flocculated yeasts, wherein the separation uses a first centrifugation and a second centrifugation, wherein the first centrifugation receives a first input liquid and produces a first output solids and a first supernatant, wherein the second centrifugation receives a second input liquid and produces a second output solids and a second supernatant, wherein the first input liquid is the fermentation broth, wherein the first centrifugation has a cut size between 10 microns and 15 microns, wherein the first output solids are fermentation coproducts, wherein the first supernatant is the second input liquid, wherein the second centrifugation has a cut size between 1.5 microns and 2.5 microns, and wherein the second output solids are the recycled yeasts.

Corn ethanol and grain ethanol production often have a significant amount of solids after fermentation which are valuable coproducts. This embodiment uses differential centrifugation to separate coproducts in the first centrifugation and to separate yeasts in the second centrifugation. This embodiment is used when the yeasts aren't flocculated, and thus have a size between 2.5 microns and 15 microns.

In some embodiments, the yeasts comprise flocculated yeasts, wherein the separation uses a high-shear defloccu-lation, a first centrifugation and a second centrifugation, wherein the high-shear deflocculation receives a high-shear input liquid and produces a high-shear output liquid, wherein the first centrifugation receives a first input liquid and produces a first output solids and a first supernatant, wherein the second centrifugation receives a second input liquid and produces a second output solids and a second supernatant, wherein the high-shear input liquid is the fermentation broth, wherein the Kolmogorov length scale of the high-shear deflocculation is between 7 microns and 15 microns, wherein the first input liquid is the high-shear output liquid, wherein the first centrifugation has a cut size between 10 microns and 15 microns, wherein the first output solids are fermentation coproducts, wherein the first supernatant is the second input liquid, wherein the second centrifugation has a cut size between 1.5 microns and 2.5 microns, and wherein the second output solids are the recycled yeasts.

When the yeasts are flocculated, certain embodiments utilize a high-shear treatment to defloculate the yeasts, and then utilize differential centrifugation to separate coproducts in the first centrifugation and to separate yeasts in the second centrifugation.

EXAMPLE

The following example demonstrates the principles of the disclosed invention. This invention, as described above, has been shown by experimental evidence to be useful for contamination control when growing yeasts.

In this example, two separate glass vessels with 400 mL of defined media were both inoculated with equal amounts of *Candida utilis* Y-264 and *Lactobacillus fermentum* B-8183. No stainless steel was in contact with either fermentation broth, and a ceramic bubbler was used to oxygenate the fermentation broth for 24 hours while the vessels were kept at 34° C. in a water bath. The carbon source in each vessel was 2.8 g of glucose and 0.05, 0.05, and 0.10 g urea was added to each vessel at the start of fermentation, after 4 hours, and after 8 hours, respectively. The defined media in both vessels comprised distilled water with 200 mg/L $KH_2PO_4$, 7 mg/L $ZnSO_4$, 4 mg/L $CuSO_4$, 20 mg/L $FeSO_4$, 5 mg/L $MnSO_4$, and 100 mg/L $MgSO_4$. Only one thing was different between the first and second vessel—the second vessel had 10 mg/L of $NiCl_2$ added.

After 24 hours of aerobic fermentation, the optical density of the first vessel increased from 0.132 to 2.025 and the optical density of the second vessel increased from 0.084 to 1.96. Previous tests showed that this fermentation entered stationary state (used up all the glucose) after 15 hours. Examination under a microscope showed that the first vessel (without added $NiCl_2$) contained mostly *Candida utilis* and the second vessel (with added $NiCl_2$) contained mostly *Lactobacillus fermentum*.

Other tests showed that adding all the urea at time 0 caused the pH of the solution to rise from about 6 to about 7, while adding the urea over time caused the pH to drop from about 5 to 4. This demonstrates that urea is preferably added at a rate that doesn't cause the pH to rise, since this is an indication that ammonia is being excreted by yeast (and bacteria can grow on ammonia).

This example clearly demonstrates that when urea is the nitrogen source and when no sources of nickel are present during fermentation, *Candida utilis* (a yeast) grows faster than *Lactobacillus fermentum* (a bacteria), thereby preventing bacterial contamination.

In this detailed description, reference has been made to multiple specific exemplary embodiments of the invention. These embodiments are described to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments and variations described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims. In the case of conflict in definitions between the present disclosure and a dictionary or other reference, the present disclosure will be controlling.

I claim:

1. A method for contamination control when growing yeasts, the method comprising growing yeasts for a fermentation time at a starting pH in a fermentation broth consisting essentially of a carbon source, urea as primary nitrogen source, a mineral source, said yeasts, and contaminating *Lactobacillus* bacteria, wherein said yeasts belong to the class *Saccharomyces*, wherein the amount of nickel in said fermentation broth is less than 1 mg/kg during the entirety of said fermentation time, wherein the growth rate of said yeasts is higher than the growth rate of said contaminating bacteria during said entirety of said fermentation time, and wherein said urea is introduced to said fermentation broth via fed-batch over time, controlling urea fed-batch feed rate such that the pH of said fermentation broth does not rise, due to addition of said urea, during said entirety of said fermentation time, wherein said method uses separation of said yeasts from said fermentation broth to produce recycled yeasts, wherein said recycled yeasts are not washed with acid after said separation; and wherein said yeasts comprise flocculated yeasts, wherein said method uses separation of said flocculated yeasts from said fermentation broth to produce recycled yeasts, wherein said separation uses a high-shear deflocculation, a first centrifugation and a second centrifugation, wherein said high-shear deflocculation receives a high-shear input liquid and produces a high-shear output liquid, wherein said first centrifugation receives a first input liquid and produces a first output solids and a first supernatant, wherein said second centrifugation receives a second input liquid and produces a second output solids and a second supernatant, wherein said high-shear input liquid is said fermentation broth, wherein the Kolmogorov length scale of said high-shear deflocculation is between 7 microns and 15 microns, wherein said first input liquid is said high-shear output liquid, wherein said first centrifugation has a cut size between 10 microns and 15 microns, wherein said first output solids are fermentation coproducts, wherein said first supernatant is said second input liquid, wherein said second centrifugation has a cut size between 1.5 microns and 2.5 microns, and wherein said second output solids are said recycled yeasts.

2. The method of claim 1, wherein said fermentation broth is in operable communication with a heat exchanger, wherein said heat exchanger is a plate heat exchanger comprising titanium heat exchange plates, and wherein said titanium heat exchange plates contain less than 1 g/kg nickel.

3. The method of claim 1, wherein said fermentation broth is in operable communication with a heat exchanger, wherein said heat exchanger is a spiral plate heat exchanger comprising titanium heat exchange plates, and wherein said titanium heat exchange plates contain less than 1 g/kg nickel.

4. The method of claim 1, wherein said method produces ethanol in said fermentation broth.

5. The method of claim 4, wherein said method further comprises distillation of said fermentation broth to separate said ethanol, and wherein the ratio of the amount of said carbon source to the amount of said urea is selected to ensure that essentially no urea remains in said fermentation broth feeding into said distillation.

6. The method of claim 1, wherein said separation uses centrifugation that receives an input liquid and produces output solids and a supernatant, wherein said input liquid is said fermentation broth, wherein said centrifugation has a cut size between 1.5 microns and 2.5 microns, and wherein said output solids comprise said recycled yeast.

* * * * *